US008728540B2

(12) United States Patent
Bolkan et al.

(10) Patent No.: US 8,728,540 B2
(45) Date of Patent: May 20, 2014

(54) STABLE AQUEOUS SOLUTIONS OF SILANE QUAT AMMONIUM COMPOUNDS

(75) Inventors: Steven Bolkan, Hopewell, NJ (US); Christine Beneciuk, Pine Beach, NJ (US); Melvin H. Czechowski, Landenberg, NJ (US); Mark Ventura, Freehold, NJ (US); David Stott, Newtown, PA (US); Nicole Nguyen, Lawrenceville, NJ (US); Steven T. Adamy, Lawrenceville, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 203 days.

(21) Appl. No.: 13/281,902

(22) Filed: Oct. 26, 2011

(65) Prior Publication Data
US 2012/0070481 A1 Mar. 22, 2012

Related U.S. Application Data

(63) Continuation-in-part of application No. 12/518,858, filed as application No. PCT/US2007/087461 on Dec. 13, 2007.

(60) Provisional application No. 60/870,038, filed on Dec. 14, 2006, provisional application No. 60/870,041, filed on Dec. 14, 2006.

(51) Int. Cl.
*A01N 59/00* (2006.01)
*C08K 5/54* (2006.01)
*C11D 3/37* (2006.01)

(52) U.S. Cl.
USPC ........... 424/717; 427/387; 510/181; 510/199; 510/240; 510/259; 510/466; 524/156

(58) Field of Classification Search
USPC ........... 424/717; 427/387; 510/181, 199, 240, 510/259, 466; 524/156
See application file for complete search history.

(56) References Cited

U.S. PATENT DOCUMENTS

| 3,622,378 | A | * | 11/1971 | Proffitt, Jr. | 428/395 |
|---|---|---|---|---|---|
| 5,281,414 | A | | 1/1994 | Stockel et al. | |
| 5,322,532 | A | | 6/1994 | Kurtz | |
| 5,588,901 | A | | 12/1996 | Rubey et al. | |
| 6,461,537 | B1 | | 10/2002 | Turcotte et al. | |
| 6,994,890 | B2 | | 2/2006 | Ohlhausen et al. | |
| 2002/0040092 | A1 | | 4/2002 | Siddiqui et al. | |
| 2002/0111282 | A1 | | 8/2002 | Charaf et al. | |
| 2003/0175438 | A1 | * | 9/2003 | Reeve | 427/387 |
| 2010/0028265 | A1 | | 2/2010 | Bolkan et al. | |
| 2010/0028462 | A1 | * | 2/2010 | Bolkan et al. | 424/717 |

FOREIGN PATENT DOCUMENTS

| EP | 0631999 | | 9/1997 | | |
|---|---|---|---|---|---|
| EP | 0733607 | | 1/2000 | | |
| EP | 1116813 | | 7/2001 | | |
| GB | 2340501 | | 7/2002 | | |
| GB | 2340502 | | 8/2002 | | |
| GB | 2407581 | | 5/2005 | | |
| JP | 55-112376 | * | 8/1980 | ........... | D06M 13/02 |
| JP | 55-112376 | A * | 8/1980 | | |
| JP | 55112376 | A * | 8/1980 | ........... | D06M 13/02 |
| JP | 60-048908 | * | 3/1985 | ........... | A01N 55/00 |
| JP | 60-048908 | A * | 3/1985 | | |
| JP | 60048908 | A * | 3/1985 | ........... | A01N 25/04 |
| JP | 03269165 | | 11/1991 | | |
| WO | 9626260 | | 8/1996 | | |

OTHER PUBLICATIONS

ÆGIS Environments, "ÆEGIS Microbe Shield™ Program—AEM 5772 Antimicrobial", MSDS, May 11, 2004.*
JP 60-048908 A, Mar. 16, 1985, USPTO translation.*
Muhammad Awais Imran, Technical Terms of Textile Dyeing, 2004-2013, Textile Learner Blog, pp. 1-20; cited as <http://textilelearner.blogspot.com/2013/04/technical-terms-of-textile-dyeing.html>.*

* cited by examiner

Primary Examiner — Jane C Osweki

(57) ABSTRACT

Textiles coated with aqueous compositions of silane quaternary ammonium compounds and alkali metal bicarbonates are provided with deodorization properties and protection from allergens, irritants, molds, dust mites, bacteria, and fungi.

26 Claims, No Drawings

STABLE AQUEOUS SOLUTIONS OF SILANE QUAT AMMONIUM COMPOUNDS

CROSS-REFERENCE TO RELATED APPLICATIONS

This application is a continuation-in-part of U.S. Ser. No. 12/518,858, filed Dec. 13, 2007, which is related to U.S. Provisional Patent Application Ser. No. 60/870,038 filed Dec. 14, 2006 and takes priority therefrom. The present application also expressly incorporates by reference herein the entire disclosure of U.S. Provisional Patent Application No. 60/870,041, filed Dec. 14, 2006 entitled "Water-Soluble Media Containing Anti-Microbial Agents".

FIELD OF THE INVENTION

The present invention relates to methods of treating surfaces to kill and/or prevent fungi and bacteria growth and protect from allergens by applying onto the surface a novel aqueous silane quaternary ammonium composition.

DESCRIPTION OF THE PRIOR ART

Concern about indoor exposure to mold has been increasing as the public becomes aware that exposure to mold can cause a variety of adverse health effects and symptoms. Molds can cause unwanted odors, produce allergens that can trigger allergic reactions or even asthma attacks in people allergic to mold. Other molds are known to produce potent toxins and/or irritants. Potential health concerns are an important reason to prevent mold growth and to remediate/clean up any existing indoor mold growth. Molds can also hasten the deterioration of surfaces and structural components of buildings.

Molds reproduce by making spores that usually cannot be seen without magnification. Mold spores waft through the indoor and outdoor air continually. When mold spores land on a damp area, the spores may begin growing and digesting whatever media such as spores are growing on in order to survive. Molds gradually destroy the area on which the spores grow.

Mold spores can be found in the air and on nearly every surface in a home, but generally a consistent source of moisture is required for mold to grow. Molds can grow on virtually any organic substance, as long as moisture and oxygen are present. There are molds that can grow on wood, paper, ceramic, concrete, plastics, textiles, and foods.

Many types of molds exist. Molds such as mold, fungus mold, and slime molds are most often found in areas that have high humidity levels such as bathrooms, kitchens, laundry rooms or damp basements (especially after flooding). Outdoor structures that are often wetted or remain damp are also areas of mold growth. Thus, roofs, fences, porches, pools and the like are often damaged by continual mold growth. Molds are a type of microscopic fungus that can grow naturally indoors and outdoors. The most common household mold types include *Aspergillus, Cladosporium, Penicillium* and *Alternaria. Stachybotrys chartarum*, often referred to as black mold, is less common than the molds listed above and is the type of mold commonly dealt with in home remediations.

Antimicrobial agents are chemical compositions that are used to prevent microbiological contamination and deterioration of products, materials, and systems. Of the diverse categories of antimicrobial agents and compositions, quaternary ammonium compounds represent one of the largest of the classes of agents in use. At low concentrations, quaternary ammonium type antimicrobial agents are bacteriostatic, fungistatic, algistatic, sporostatic, and tuberculostatic. At medium concentrations they are bactericidal, fungicidal, algicidal, and viricidal against lipophilic viruses. Silicone containing quaternary ammonium compounds are well known as exemplified by U.S. Pat. No. 3,560,385, and the use of such compounds as antimicrobial agents is taught, for example, in a wide variety of patents such as U.S. Pat. Nos. 3,730,701, and 3,817,739, where the compounds are used to inhibit algae; U.S. Pat. Nos. 3,794,736 and 3,860,709 where they are employed for sterilizing or disinfecting a variety of surfaces and instruments; U.S. Pat. No. 3,865,728, where the compounds are used to treat aquarium filters; U.S. Pat. No. 4,259,103; and in British Patent No. 1,386,876. Published unexamined European Application No. 228464 of Jul. 15, 1987, teaches that microorganisms on plants can be killed by the application thereto of an aqueous mixture of a surfactant and an organosilicon quaternary ammonium compound. In a particular application of an antimicrobial silicone quaternary ammonium compound, a paper substrate is rendered resistant to the growth of microorganisms in U.S. Pat. No. 4,282,366. In U.S. Pat. No. 4,504,541, an antimicrobial fabric is disclosed which is resistant to discoloration and yellowing by treatment of the fabric with a quaternary ammonium base containing an organosilicone. U.S. Pat. No. 4,516,937, as well as its companion U.S. Pat. No. 4,692,374, relate to wet wiper towelettes having an antimicrobial agent substantive to the fibers of the web and being an organosilicon quaternary ammonium compound. In a series of patents assigned to Burlington Industries, Inc. U.S. Pat. Nos. 4,408,996, 4,414,268, 4,425,372, and 4,395,454, such compounds are disclosed to be useful in surgical drapes, dressings, and bandages. This same assignee also discloses these compounds as being employed in surgeons' gowns in U.S. Pat. Nos. 4,411,928 and 4,467,013. Organosilicon quaternary ammonium compounds have been employed in carpets in U.S. Pat. No. 4,371,577; applied to walls, added to paints, and sprayed into shoes, in U.S. Pat. No. 4,394,378; applied to polyethylene surfaces and used in pillow ticking in U.S. Pat. No. 4,721,511; in flexible polyurethane foams of fine-celled, soft, resilient articles of manufacture in U.S. Pat. No. 4,631,297; and mixed with a nonionic surfactant in Japanese Kokai Application No. 60-048908, filed Aug. 26, 1983, of Sanyo Chemical Industries, Ltd., for the purpose of achieving uniformity of distribution of compounds to a textile surface. Thus the versatility of such compositions is readily apparent.

For organosilanes $R_nSiX_{4-n}$, where n is an integer from 0 to 2, hydrolysis of the first two X groups with water produces a species bearing —$Si(OH)_2$— units which can self-condense through the hydroxyl moieties to linear and/or cyclic oligomers possessing the partial structure HO—Si—(O—Si)$_{mm}$—O—Si—O—Si—O—Si—OH, where mm is an integer such that an oligomer is formed. For those cases, $RSiX_3$, hydrolysis of the third X group generates a silanetriol ($RSi(OH)_3$) which produces insoluble organosilicon polymers through linear and/or cyclic self-condensation of the Si(OH) units. This water induced self-condensation generally precludes storage of most organosilanes $R_nSiX_{4-n}$, where n ranges from 0 to 2, inclusive, in water. Except for some organosilanes which can be stable in very dilute solutions at specific pH ranges, the use of water solutions of most organosilanes require the use of freshly prepared solutions. Quaternary ammonium organosilanes are often applied from solvent solutions such as lower alcohols and the commercial versions of these quaternized organosilanes are commonly provided as methanolic solutions.

Quaternary ammonium functional organosilanes containing hydrolyzable groups such as those sold under the trademark AEM® 5772 (3-(trimethoxysilyl)propyldimethyloctadecyl ammonium chloride) by Aegis Environmental Co. of Midland, Mich. and REQUAT® 1977 (3-(trimethoxysilyl) propylmethyldi(decyl)ammonium chloride) by Sanitized, Inc. of New Preston, Conn. have found a large number of uses because of their ability to attach themselves to a wide variety of substrates where the quaternary ammonium functional group then acts as an antimicrobial and algicidal agent. Substrates treated with such quaternized organosilanes have also been noted to, among other things, be easier to clean, possess soil release properties, and cause hair to exhibit a conditioned appearance.

A clear microemulsion of a quaternized organosilane using a cosurfactant having an HLB value of at least 1 is taught in U.S. Pat. No. 4,842,766 to Blehm et al. This patent teaches that the methanol-based solvent in which the organosilane is supplied must be removed before blending the quaternized organosilane with the cosurfactant (e.g., a nonionic surfactant can used). If the methanol is not removed, a creamy white emulsion forms which is unstable and will separate into oil and water phases over time. The '766 patent also teaches that high shear may have to be applied to the mixtures of organosilane and cosurfactant to ensure codispersion.

Obviously, this has the disadvantage of requiring a homogenization step to prepare such microemulsions. Blehm et al. teach that almost any surfactant can be employed including anionic, cationic, amphoteric or zwitterionic surfactants as well as nonionic surfactants although nonionic surfactants and compounds such as glycerol, ethylene glycol, propylene glycol and higher monoalcohols such as pentanol, decanol and decanediol are most preferred.

Another patent teaching oil-in-water emulsions containing 3-(trimethoxysilyl)propyldimethyloctadecyl ammonium chloride as well as, optionally, cosurfactants such as nonionic and cationic surfactants, is U.S. Pat. No. 4,631,273 to Blehm et al. These emulsions employ a homogenizer using high shear conditions and teach that the quaternized organosilane does not hydrolyze while it is in emulsion form and thus does not polymerize to an insoluble siloxane. The Examples use ARQUAD® T27W cationic surfactant which is trimethyl tallow ammonium chloride. However, these emulsions also require a water immiscible liquid such as a polydimethylsiloxane or a mineral oil with which the quaternized organosilane associates. Blehm et al. teach that a sufficient shear force is necessary to form the emulsions and that an Eppenbach mixer did not provide a sufficient amount of such shear.

Therefore, there exists a need for extended shelf life, water-stable organosilane compounds, such as silane quaternary ammonium compounds, products and compositions thereof that, upon application, the active portion of the organosilane is operative for the selected application. Moreover, there exists a need for water-stable, organosilane quaternary ammonium compounds, products and compositions which are essentially non-toxic, non-flammable, uniformly dispersable, and simple and economical to manufacture and use.

SUMMARY OF THE INVENTION

The present invention relates to an aqueous composition comprising an organosilane quaternary ammonium component, and an alkali bicarbonate component for treating a surface susceptible to fungi and bacteria growth, and to protect from the deposition of allergens on the surface. The aqueous composition of this invention is devoid of other polysiloxanes, has a long, stable shelf life, can be readily applied to any surface, and dries quickly once applied. The composition can be made by directly mixing the alcoholic solution of the organosilane quaternary compound to water without the need for removing the alcohol. Once in solution, the composition remains stable even if exposed to air until it is applied, and then dries quickly. The optional addition of surfactant allows the composition to be applied evenly across any surface. The alkali metal bicarbonate improves the antimicrobial properties of the composition and improves the drying time of the applied composition. The composition can be applied to a surface by any conventional coating method, such as by spraying, dipping wiping, roller coating and the like.

DETAILED DESCRIPTION OF THE INVENTION

The film-forming, organosilicone quaternary ammonium compounds which find use in the present inventive antimicrobial compositions include those which may be represented by the following structural representation:

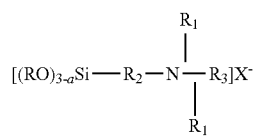

wherein:

R is an independent short chain alkyl group, preferably $C_1$-$C_4$ alkyl, or hydrogen, and a is 0, 1, or 2;

$R_1$ and $R_2$ each independently represents short chain alkyl or alkenyl groups, preferably $C_1$-$C_8$ alkyl or alkenyl groups;

$R_3$ represents a $C_{11}$-$C_{22}$ alkyl group; and

X represents a salt forming counterion, especially a halogen.

Preferred short chain alkyl substituents for R and $R_1$ are methyl and ethyl. Preferred short chain alkyl substituents for $R_2$ are straight chain links of methylene groups consisting of from 1 to 4 members. Preferred $R_3$ substituents are straight chain links of methylene groups consisting of from 11 to 22 members, and preferred halogens for X are chloride and bromide. More preferably, both $R_1$ groups are methyl.

A particularly useful film-forming, organosilicone quaternary ammonium compound useful in the inventive compositions is AEM® 5772 or AEM® 5700 (from Aegis Environmental Co., Midland, Mich.). Both of these materials are described as being 3-(trimethoxysilyl)propyloctadecyldimethylammonium chloride. AEM® 5700 is sold as a 42% by weight active solution of the compound in methanol, while AEM® 5772 is sold as a 72% by weight active solution of the compound in methanol.

The term "antimicrobial" as used herein is used in reference to the ability of the compound composition or article to eliminate, remove, inactivate, kill or reduce microorganisms such as bacteria, viruses, fungi, molds, yeasts and spores. The term antimicrobial as used herein to imply reduction and elimination of the growth and formation of microorganisms such as described above.

Specific non-limiting quaternary ammonium organosilanes within the scope of the invention are represented by the formulae:

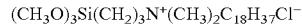

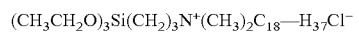

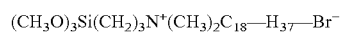

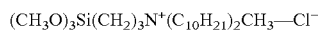

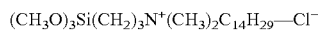

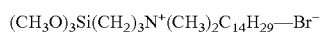

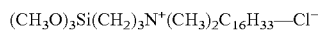

Other useful quaternary ammonium organosilanes of the present invention are 3-(trimethoxysilyl)propyldimethyloctadecyl ammonium chloride and 3-(trimethoxysilyl)propyldidecylmethyl ammonium chloride.

The film-forming, organosilicone quaternary ammonium compounds are desirably present in the inventive compositions in amounts of from 0.1 to 5.0% by weight, preferably in amounts of from 0.2 to 4.0% wt., and most preferably from 0.3 to 1.0% by weight, based on the total weight of the aqueous composition of which it forms a part. The compositions will contain a small amount of an organic solvent for the organosilicone quaternary ammonium compounds. As previously noted, the organosilicone quats are typically marketed in methanol. While methanol is a preferred solvent, other lower alcohols, $C_1$ to $C_4$, can be used. Typically, the solvent will be present in amounts of about 10 to 50% by weight of the silane quat.

Suitable nonionic surfactants that can be added to the composition include the polyoxyethylene-polyoxypropylene condensates, which are sold by BASF under the tradename "Pluronic", polyoxyethylene condensates of alkyl phenols; polyoxyethylene condensates of aliphatic alcohols/ethylene oxide condensates having from 1 to 30 moles of ethylene oxide per mole of coconut alcohol; ethoxylated long chain alcohols sold by Shell Chemical Co. under the tradename "Neodol," or sold by Sasol North America, Inc. under the tradename "Novel," polyoxyethylene condensates of sorbitan fatty acids, sorbitan dialkylesters, sorbitan alkylesterethylene glycol condensates, aliphatic alcohol polyethylene glycol condensates, alkylphenol polyethylene glycol condensates, polypropylene glycol polyethylene glycol condensates, alkanolamides, such as the monoalkoanolamides, dialkanolamides and the ethoxylated alkanolamides, for example coconut monoethanolamide, lauric isopropanolamide and lauric diethanolamide; and amine oxides for example dodecyldimethylamine oxide.

Suitable nonionic surfactants also include, inter alia, condensation products of alkylene oxide groups with an organic hydrophobic compound, such as an aliphatic compound or with an alkyl aromatic compound. The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water soluble nonionic detergent. Further, the length of the polyethenoxy hydrophobic and hydrophilic elements may be varied to adjust these properties.

An example of such a nonionic surfactant is the condensation product of one mole of an alkylphenol having an alkyl group containing from 6 to 12 carbon atoms with from about 5 to 25 moles of an alkylene oxide. Another example of such a nonionic surfactant is the condensation product of one mole of an aliphatic alcohol which may be a primary, secondary or tertiary alcohol having from 6 to 18 carbon atoms with from 1 to about 10 moles of alkylene oxide. Suitable alkylene oxides can be either ethylene oxides or propylene oxides or mixtures thereof.

Suitable nonionic surfactants also include primary and secondary linear and branched alcohol ethoxylates, such as those based on $C_{10}$ to $C_{16}$ alcohols which further include an average of from 3 to 10 moles of ethoxylation per mol of alcohol Particularly preferred nonionic surfactants are $C_{11}$ linear primary alcohol ethoxylates averaging about 9 moles of ethylene oxide per mole of alcohol. These surfactants are available, for example, under the commercial name of Neodol 1-9, (from Shell Chemical Company, Houston, Tex.), or in the Genapol® series of linear alcohol ethoxylates, particularly Genapol®. 26-L-60 or Genapol®. 26-L-80 (from Clariant Corp., Charlotte, N.C.). A further class of nonionic surfactants which are advantageously present in the inventive compositions are those presently marketed under the Genapol® trade name. Particularly useful are those in the Genapol® "26-L" series which include for example: $C_{12-16}$ linear alcohols condensed with 1 mole of ethylene oxide (Genapol® 24-L-3); $C_{12-16}$ alcohols condensed with 1.6 moles of ethylene oxide (Genapol® 26-L-1.6); $C_{12-16}$ linear alcohols condensed with 2 moles of ethylene oxide (Genapol® 26-L-2); $C_{12-16}$ linear alcohols condensed with 3 moles of ethylene oxide (Genapol® 26-L-3); $C_{12-16}$ linear alcohols condensed with 5 moles of ethylene oxide (Genapol® 26-L-5); as well as $C_{12-16}$ linear alcohols condensed with varying amounts of ethylene oxide to provide specific cloud points of the surfactant (i.e., Genapol® 26-L-60, Genapol® 26-L-60N, and Genapol® 26-L-98. These materials are commercially available from Clariant Corp. (Charlotte, N.C.).

It is to be understood that nonionic surfactants other than those described above may also be used. By way of illustration, and not by way of limitation, examples include secondary $C_{12}$ to $C_{15}$ alcohol ethoxylates, including those which have from about 3 to about 10 moles of ethoxylation. Such are available in the Tergitol® series of nonionic surfactants (Dow Chemical Co., Midland, Mich.), particularly those in the Tergitol® "15-S-" series. Further exemplary nonionic surfactants include linear primary $C_{11}$ to $C_{15}$ alcohol ethoxylates, including those which have from about 3 to about 10 moles of ethoxylation. Such are available in the Neodol[1]® series of nonionic surfactants (Shell Chemical Co.) N-alkyl pyrrolidones such as marketed under the tradename "Surfadone," ISP Investment Corp., Wayne, N.J. are also useful.

Flurosurfactants can also be used. Preferably, the fluorinated surfactant for use in the present invention is a fluorinated hydrocarbon. Examples of fluorinated surfactants for use in the present invention include Zonyl FSO Fluorosurfactant (described as a perfluoroalkyl ethoxylate) available from E. I. DuPont de Nemours & Co., Inc., and Fluorad FC-430 surfactant (described as a fluoroaliphatic polymeric ester) available from the Industrial Chemical Products Division of 3M.

It may also be useful to incorporate an anionic surfactant to the composition. Anionic surfactants are useful in providing a cleaning function and an anti-redeposition function to the composition. Further, if a foaming action may be useful, an anionic surfactant can provide for such foaming. However, the high degree of hydrophobicity, and the cationic charge of the useful silane quaternary compounds used in the composition make it difficult to formulate such materials into an aqueous system when anionic surfactants are present. It has been found, however, that system employing anionic surfactants of polyethylene glycol ethers of fatty alcohols esterified with sulfuric acid can be useful and provide homogenous aqueous systems with the silane quaternary compounds used in this invention. Fatty alcohols containing at least 12 carbon atoms etherified with at least 12 alkylene oxide groups can be used. For example, laureth sulfates containing at least 12 ethoxy groups can yield homogenous aqueous systems. Laureth-30 sulfate has been found to be particularly useful in providing homogenous aqueous systems containing the useful quaternary ammonium silane compounds of this invention, used to impart anti-microbial properties to surfaces.

The amount of surfactant needed to provide a stable aqueous composition and allow the composition to be readily applied to a substrate and flow evenly thereon is relatively minor. In general, the relative ratio of organosilane quaternary ammonium compound to surfactant will range from about 10:1 to 1:<3.0 by weight. Weight ratios of the silane quaternary antimicrobial active to surfactant of 1:1 to 1:2 are also exemplified.

The compositions of the present invention can also include an alkali metal salt such as sodium and potassium bicarbonates. In general, the bicarbonate salt is added to improve the antimicrobial properties and reduce the drying time of the composition once the composition is applied to a surface. The bicarbonate salt is added in amounts ranging from 0.1 to 10 wt. % relative to the weight of the composition. Amounts ranging from 0.1 to 7 wt. %, 0.1 to 5 wt. %, 0.1 to 1 wt.%, 0.1 to 0.5 wt. % and 0.15 to 10 wt. % are also exemplified. The bicarbonate salt can be added directly to the aqueous silane quaternary composition and mixed therein. Alternatively, a solid surface, such as a surface containing fungi, such as mold, or susceptible to mold growth, can be blast cleaned with a bicarbonate abrasive such as Armex®, marketed by the assignee, and the aqueous composition containing the silane quaternary ammonium applied to the blast cleaned surface. Residual bicarbonate salt that remains on the surface after blast treatment becomes part of the aqueous coating and aids in the antimicrobial effect of the coating composition.

The compositions of this invention comprise and dilute aqueous solutions which have high water content. Typically the compositions will contain at least 80 wt. % water. Water content of up to 99 wt. % is also exemplified.

The composition according to the present invention can be provided as a ready to use product in a pressurized container or in a manually operated spray dispensing container and is suitable for use in a consumer "spray and wipe" application. The composition can be applied to the surface as an aerosol or finely divided atomized spray. The composition can also be applied by any type of applicator such as brush, roller, sponge, etc. Articles can also be coated with the compositions of this invention by dipping or immersing the article into the composition.

Whereas the compositions of the present invention are intended to be used in the types of liquid forms described above, nothing in this specification shall be understood as to limit the use of said compositions with a further amount of water to form a cleaning solution. In such a proposed diluted cleaning solution, the greater the proportion of water added to form said cleaning dilution, the greater may be the reduction of the rate and/or efficacy of the inventive compositions. Accordingly, longer residence times upon the surface and/or the usage of greater amounts may be necessitated. Conversely, nothing in the specification shall be also understood to limit the forming of a "super-concentrated" cleaning composition based upon the composition described above. Such super-concentrated ingredient compositions are essentially the same as the cleaning compositions described above except in that they include a lesser amount of water.

The composition of the present invention can be used to treat any surface which is susceptible to antigens, such as fungi, bacteria and allergens, or in which such antigens are already present in order to prevent or kill antigens that are present. The invention is particularly useful in killing and preventing the further growth of fungi, bacteria and allergens on any and all exterior and interior building surfaces. Such surfaces can be formed of any material onto which the antigens may grow, in particular when such surfaces become wet and can remain damp for a significant period of time. Thus, the composition can be applied to metal, masonry, stucco, plaster, paper, wood, ceramic, glass, plastics, natural or synthetic fiber, etc. Interior surfaces such as formed from ceramic tile, which is spaced by a plaster-type grout, can also be effectively treated with the composition of this invention. The composition can be applied to filters such as used to remove particulates from an air stream for heating or cooling an interior space. It is believed that application to the filters would kill any mold spores captured within the filter medium, thus preventing the spread of mold through the interior environment.

The compositions according to the present invention can be applied to surfaces, such as lavatory fixtures and lavatory appliances (toilets, bidets, shower stalls, bathtubs and bathing appliances), swimming pools, wall and flooring surfaces especially those which include refractory materials and the like. The compositions can be applied to surfaces associated with kitchen environments and other environments associated with food preparation, to surfaces associated with hospital environments, medical laboratories and medical treatment environments.

The composition of the present invention can be used to treat surfaces of personal items, such as a tooth brush, a comb, a hair brush, dentures, an orthodontic retainer and the like.

The composition of the present invention are useful for treating concrete structures such as livestock shelters, where microbial infestation is a problem, concrete pipe, and the like.

The compositions of the present invention are useful for treating surfaces and substrates, which include, but are not limited to, textiles, carpet, carpet backing, upholstery, curtains, drapes, clothing, gloves, hosiery, bedding, mattress piling, intimate apparel, underwear, outerwear apparel, shoes, socks, towels, bandages, gauze, and the like. Examples of fibers and fabrics therefrom, which can be treated include any natural or synthetic materials, such as, but not limited to, cotton, wool, bamboo, hemp, polyester, nylon, rayon and fabric blends, etc. In general, the amount of coating applied will range from about 20-250 wt. % of the substrate on a wet basis. Typically, the amount of coating on a wet basis will range from about 25-100 wt. % of the substrate.

The composition can also be applied to a rinse cycle of a laundry machine cycle to treat fabrics and clothing normally washed in a wash cycle.

The compositions of the present invention are useful for treating surfaces and substrates, which include, but are not limited to sponges, containers, trash receptacles, tiles, floors, marine products, outdoor gear, tents, backpacks, tarpaulins, sails, ropes, and the like.

The compositions of the present invention are useful for treating surfaces and substrates, which include, but are not limited to, air filters, as mentioned previously, as well as materials used for the manufacture thereof, aquarium filters, swimming pool filters, and the like.

The composition of the present invention can be used to treat various building construction materials, which include, but are not limited to, wood products, masonry, vinyl or aluminum siding, roofing, roofing shingles, fiberglass insulation, fiberglass ductboard, fencing, trim, insulation, wallboard and the like.

The composition of the present invention can be used to treat polyurethane and polyethylene foam, sand bags, and non-food or food contacting surfaces in general.

The composition can be made into a castable powder which can be applied to carpet, draperies, upholstery, furniture and the like and which thereafter can be removed by vacuuming.

The composition of the present invention can be used to treat textile goods (woven and non-woven) and yarns (synthetic and natural).

The composition of the present invention can be used to treat latex medical articles, surgical gloves, surgical dressings, sponges and the like.

The following examples are for the purpose of illustrating the invention and are not to be construed as strictly limiting the invention to only the illustrated embodiments.

Example 1

A composition was prepared comprising:
1.0% AEM 5772[1] (Aegis Antimicrobial agent)
0.05% Zonyl FSH (fluorsurfactant)
0.1% Sasol 23 E7 (ethoxylated alcohol)
98.85% Water
1. AEM 5772 is a composition as follows (all amounts are % by weight): 12% Methanol 72% 3-(trihydroxysilyl)propyldimethyl-octadecyl ammonium chloride 15% Chloropropyl trimethoxysilane 1% Dimethyl C18 amine.

The composition was applied to surfaces of the following: stainless steel, aluminum, wood, glazed tile, unglazed tile, glass, and vinyl siding. To facilitate drying, the coated articles were placed in an oven at about 122° F. The articles were taken out of the oven, cooled and rinsed with water. Each surface was coated with bromophenol blue in order to determine if the silane quat was bonded to the surface. Each coated surface turned blue, which indicated that the silane quat was bonded to the surface.

Example 2

A composition was prepared comprising:
1.0% AEM 5772 (Aegis Antimicrobial agent)
0.5% Sodium Bicarbonate
2.0% Hexyl Carbitol (diethylene glycol hexyl ether)
96.50% Water The composition was applied to surfaces of the following: stainless steel, aluminum, wood, glazed tile, unglazed tile, glass, and vinyl siding. To facilitate drying, the coated articles were placed in an oven at about 122° F. The articles were taken out of the oven, cooled and rinsed with water. Each surface was coated with bromophenol blue in order to determine if the silane quat was bonded to the surface. Each coated surface turned blue, which indicated that the silane quat was bonded to the surface. The use of sodium bicarbonate accelerates the activity of the composition and aids in the binding of the silane quat to the surfaces.

Example 3

A composition was prepared comprising:
1.0% AEM 5772 (Aegis Antimicrobial agent)
0.25% Sodium Bicarbonate
1.25% Hexyl Carbitol (diethylene glycol hexyl ether)
97.50% Water The composition was applied to surfaces of the following: stainless steel, aluminum, wood, glazed tile, unglazed tile, glass, and vinyl siding. To facilitate drying, the coated articles were placed in an oven at about 122° F. The articles were taken out of the oven, cooled and rinsed with water. Each surface was coated with bromophenol blue in order to determine if the silane quat was bonded to the surface. Each coated surface turned blue, which indicated that the silane quat was bonded to the surface.

Example 4

Four different formulas were tested in order to compare and contrast their spreading and wetting characteristics.

| FORMULA | % ACTIVE[1] | % SURFACTANT | % WATER |
| --- | --- | --- | --- |
| 1% AEGIS | 1% | 0 | 99% |
| A | 1% | 1.25% Hexyl carbitol 0.25% SBC | 97.50% |
| B | 1% | 0.1% Sasol 23 E7[2], 0.05% Zonyl FSH | 98.85% |
| Microbe Guard[3] | .75% | N/A | 99.25% |

[1]Active means the complete formula as set forth in footnote 1 in Example 1.
[2]Branched ethoxylated alcohol.
[3]Commercial formula contains AEGIS formula in water.

Tests on Wood

The first test involved placing several drops of each formula on a wood substrate. The wood substrate used was a tongue depressor stick. 5-6 drops of each formula were placed on the stick using a disposable plastic pipette.

The sticks were then immediately rinsed with water and wiped three times with a sponge and rinsed again. The sticks were set aside to dry. Once the sticks were dry, bromophenol blue "BPB" indicator was applied, to check for the presence of the quat. The anion of bromophenol blue is complexed with the cation of the polymerized silane quaternary compound; the presence of a blue color is an indication of proper antimicrobial treatment.

After allowing the BPB to saturate for 10 minutes, the sticks were then rinsed off again with water and allowed to dry. A handheld colorimeter was used to quantify which sample absorbed more of the quat. Of the L, a, and b values, b was used to quantify the intensity of the blue stain. The more negative the number the more blue the stain.

The results were as follows:

| SAMPLE | b1 | b2 | b avg. | % quat |
| --- | --- | --- | --- | --- |
| A | −11.4 | −9.2 | −10.3 | 61.86% |
| B | −7.8 | −6.8 | −7.3 | 43.84% |
| 1% Aegis | −7.9 | −6.6 | −7.25 | 43.54% |
| Microbe Guard Control | −0.8 | −2.5 | −1.65 | 9.90% |
| Stick | 17 | 18.1 | 17.55 | |
| Stained stick | −15.8 | −17.5 | −16.65 | 100% |

After an immediate rinse, formula A bound 61.68% quat, B and 1% Aegis bound 43.84% of the silane quat to the surface, and the Microbe Guard only had 9.90% of the saline quat bound to the surface.

The test was repeated except the antimicrobial formulas were allowed to cure for one minute after application to the sticks. After one minute, the samples were rinsed with water and wiped. The results follow:

| SAMPLE | b1 | b2 | bavg | % quat |
|---|---|---|---|---|
| A | −9.2 | −10.5 | −9.85 | 59.15% |
| B | −10.1 | −8.7 | −9.4 | 56.45% |
| 1% Aegis | −8.4 | −7.7 | −8.05 | 48.34% |
| Microbe Guard Control | −2.8 | −3 | −2.9 | 17.41% |
| | | | | |
| Stick | 17 | 18.1 | 17.55 | |
| Stained stick | −15.8 | −17.5 | −16.65 | 100% |

At one minute, 1% Aegis, B, and A cured equally the same. The major difference seen on the sticks was the even distribution of the silane quat on samples in which formulas A and B were applied.

Spreading

Formulas A and B demonstrated to have better surface spreading characteristics than the other two formulas tested. A visualization of the sticks having applied thereto formulas A and B, showed that the formulas were evenly spread out over each of the sticks. Formulas 1% Aegis and competitor Microbe Guard did not spread out after treatment. The drops of product remained in the area they were placed. Surface tensions and wetting times of the formulas are listed below. Initial wetting time of a freshly prepared 1% AEM 5772 solution is 45 seconds. Four hours after preparation, the wetting time extends to 12 minutes. After 24 hours, the wetting time extends to 1 hour. The wetting time for Formula A remains 0 seconds after 4 and 24 hours.

| FORMULA | SURFACE TENSION (dynes) | WETTING (seconds) Draves wetting test |
|---|---|---|
| 1% AEGIS | 42.48 | 45 |
| A | 29.25 | 0 |
| B | 27.38 | 6.74 |
| Microbe Guard | 47.85 | — |

Tests on Aluminum

Curing time and silane quat presence were of interest in this test. The substrates used were aluminum coupons. 3-4 drops of each formula were placed on the aluminum coupons with a pipette and allowed to dry for 25 minutes. A second series of tests involved coating and drying overnight. The formulas were not spread out on the aluminum. After the drops were placed on the aluminum coupons, the samples were not disturbed until the given time span expired. After the allowed cure time, the samples were then rinsed, wiped and dried. The samples were then treated with bromophenol blue indicator to check for the presence of the quat. The anion of bromophenol blue is complexed with the cation of the polymerized silane quaternary compound; the presence of a blue color is an indication of proper antimicrobial treatment. A hand held calorimeter was used to quantify the color blue present. Of the L, a, and b values, just the value b was used for this test. The b value reads the yellow/blue color. The b value is more negative the bluer the color present. A more yellow color gives a positive number. The following shows the results:

| SAMPLE | b1 | b2 | bavg | % quat |
|---|---|---|---|---|
| 1% Aegis | 1.9 | 2.7 | 2.3 | −7.60331 |
| Microbe Guard | 2 | 2 | 2 | −6.61157 |
| A | −27.5 | −31.1 | −29.3 | 96.8595 |
| B control | 2.5 | 2.8 | 2.65 | −8.76033 |
| | | | | |
| aluminum | 2.3 | 2 | 2.15 | |
| stained Al | −29 | −31.5 | −30.25 | 100 |

At 25 minutes the only formula that cured to the surface was A. All other formulas did not cure to the surface in the 25-minute time span.

Example 6

The following represents a useful formula in accordance with this invention:
1.00% AEM 5772
1.25% Hexyl Carbitol $C_6H_{13}(OCH_2CH_2)_2OH$
0.17% Sodium Bicarbonate
98.3% Water Example 7

The following represents a useful formula in accordance with this invention:
0.10% LP-100 Surfadonne
1.00% hexyl carbitol
0.17% Sodium bicarbonate
1.00% AEM 5772 Silane quat
97.73% Water Example 8

The following represents a useful formula in accordance with this invention:
1.00% AEM 5772
2.00% Butyl Carbitol (diethylene glycol butyl ether)
0.17% Sodium Bicarbonate
0.15% Surfadone LP-100 (1-octyl-2-pyrrolidone)
96.68% Water Example 9

The following example is directed to treating textile and fabric materials made therefrom. The process of this invention imports deodorization properties, protection from irritants, allergy reduction and relief, protection from mold, dust mites, bacteria and fungi, and can provide water repellency.

1 gram polyester or polyester/natural fiber blend fabric squares were treated as follows:
Test 1=
0.1%-0.4% active Aegis AEM 5772 antimicrobial solution
0.1-1% Sodium Bicarbonate
0.05-0.5% Tomadol 1-9 nonionic surfactant (C11 alcohol ethoxylate)
q.s. water
Control 1=
0.1-1% Sodium Bicarbonate
0.05-0.5% Tomadol 1-9 nonionic surfactant (C11 alcohol ethoxylate)
q.s. water
Test 2=
0.5%-0.8% active Aegis AEM 5772 antimicrobial solution
0.1-1% Sodium Bicarbonate
0.05-0.5% Tomadol 1-9 nonionic surfactant (C11 alcohol ethoxylate)

q.s. water
Control 2=
Treated with normal textile processing aides only, including 0.5-7 wt. % of a fatty alcohol ethoxylate polymer blend, 0.5-7 wt. % cationic surfactant and 86-99 wt. % water.
Analytical and Antimicrobial Testing of Treated Fabric

| Fabric | Run | Microbial Analysis (ASTM E2149-10 against e-coli) | Chemical Analysis Uniformity | % Extraction |
|---|---|---|---|---|
| 1 | Test 1 | 99.60% | Excellent | 86% |
| 1 | Control 1 | 28.00% | No Color | 8% |
| 1 | Test 2 | 99.99% | Excellent | 92% |
| 1 | Control 2 | <20%* | No Color | 2% |
| 2 | Test 1 | 99.99% | Excellent | 87% |
| 2 | Control 1 | <20% | No Color | 8% |
| 2 | Test 2 | 99.99% | Excellent | 95% |
| 2 | Control 2 | <20% | No Color | 0% |
| 3 | Test 1 | 99.99% | Excellent | 88% |
| 3 | Control 1 | 30.00% | No Color | 1% |
| 3 | Test 2 | 99.99% | Excellent | 90% |
| 4 | Test 1 | 99.99% | Excellent | 94% |
| 4 | Control 1 | <20% | No Color | 8% |
| 4 | Test 2 | 99.99% | Excellent | 97% |
| 4 | Control 2 | <20% | No Color | 4% |
| 5 | Test 1 | 99.99% | Very good | 71% |
| 5 | Control 1 | 35.00% | No Color | 0% |
| 5 | Test 2 | 99.99% | Very good | 83% |
| 5 | Control 2 | 21.00% | No Color | 0% |
| 6 | Test 1 | 99.99% | Excellent | 73% |
| 6 | Control 1 | <20% | Poor | 0% |
| 6 | Test 2 | 99.99% | Excellent | 70% |
| 6 | Control 2 | 28.00% | Poor | 0% |
| 7 | Test 1 | 86.00% | Very good | 81% |
| 7 | Control 1 | <20% | No color | 0% |
| 7 | Test 2 | 99.99% | Excellent | 90% |
| 7 | Control 2 | 23.00% | No Color | 0% |
| 8 | Test 1 | 99.99% | Very good | 78% |
| 8 | Control 1 | <20% | No Color | 0% |
| 8 | Test 2 | 99.99% | Excellent | 90% |
| 8 | Control 2 | 27.00% | No Color | 0% |

*<20% is the lowest reported within the test method

Example 10

To further demonstrate the utility of the invention, the example below shows the use of the silane quaternary ammonium compound used in combination with other processing and finishing materials. No deleterious effects were seen with the incorporation of the silane quaternary compound, either on the quality and processability of the polyester fabric nor on the quality of antimicrobial activity, as shown in the table below.
Test 1:
0.44% active Aegis AEM 5772 antimicrobial solution
0.40% sodium bicarbonate
0.4% Tomadol 1-9 nonionic surfactant (C11 alcohol ethoxylate)
Standard textile finishing Formula 1
Control 1:
0.40% sodium bicarbonate
0.4% Tomadol 1-9 nonionic surfactant (C11 alcohol ethoxylate)
Standard textile finishing Formula 1
Test 2:
0.44% active Aegis AEM 5772 antimicrobial solution
0.40% sodium bicarbonate
0.4% Tomadol 1-9 nonionic surfactant (C11 alcohol ethoxylate)
Standard textile finishing Formula 2
Control 2:
0.44% silane quaternary compound
0.40% sodium bicarbonate
0.4% Tomadol 1-9 nonionic surfactant (C11 alcohol ethoxylate)
Standard textile finishing Formula 2

| Fabric | Run | Reduction of e. coli (%) per ASTM E2149-10 | Uniformity | Active Extraction (%) |
|---|---|---|---|---|
| DP | Test 1 | 99.99% | Good | 35% |
| DP | Control 1 | <20%* | N/A | 0% |
| JA | Test 1 | 99.99% | Good | 40% |
| JA | Control 1 | <20%* | N/A | 0% |
| SI | Test 2 | 99.99% | Good | 67% |
| SI | Control 2 | <20% | N/A | 3% |

*<20% is the lowest level reported within the test method.

Example 11

A series of studies were performed in order to probe the effect of the number of ethoxy groups in laureth sulfate on the phase behavior of systems also incorporating nonionic surfactants and silane quat AEM 5772.
The surfactants used were as follows:

| Surfactant | Supplier | Description |
|---|---|---|
| Steol CS330 | Stepan | Sodium laureth-3-sulfate (AES3) |
| Polystep B 12 | Stepan | Sodium laureth-4-sulfate (AES4) |
| Polystep B23 | Stepan | Sodium laureth-12-sulfate (AES12) |
| Polystep B19 | Stepan | Sodium laureth-30-sulfate (AES30) |
| Neodol25-7 | Shell | C12-C15 ethoxylated fatty alcohol 7EO |
| AmmonyxLO | Stepan | Lauryl amine oxide (C12AO) |

The pseudo-component at each corner of a triangular phase diagram incorporated the same level of one of Neodol, Ammonyx or AES surfactants (15% actives basis) and the same level of AEM 5772 (2% as is) so that the levels of both these materials remained constant across the entire diagram. A sodium bicarbonate buffer was also included in each sample. Diagrams were constructed by preparing a series of samples of 10 g each in glass screw-top culture tubes. The samples were initially mixed by vortexing for about 20 seconds. Following preparation, the samples were allowed to equilibrate for a minimum of 48 hours at room temperature (about 25° C.). The tubes were then visually examined for the presence of one or more phases. The characteristics were then recorded. Lines of division were then drawn on the diagrams between dissimilar phases.

In systems incorporating AES3 and AES4, very small one-phase regions were observed bordering the Ammonyx LO-Neodol 25-7 side. Upon increasing the number of EO groups of the sodium laureth sulfate to 12, the size of the one-phase region expanded to cover about half of the phase diagram. Upon increasing the EO number to 30, all compositions were generally one-phase. Compositions along the AES30-N25-7 border may have exhibited a very fine dispersed phase, but it was very difficult to see.

Levels of AEM 5772 were then increased to 4% in systems with AES12 and AES30. Systems with increasing levels of AEM 5772 were formed by directly adding AEM 5772 to existing tubes. The tubes were re-mixed by vortexing and allowed to sit for 48 hours minimum. The process was repeated as required. The mutt-phase liquid+precipitate regions increased some in the AES 12 system, although the AES30 system remained homogenous.

Finally, AEM 5772 was added to the AES30 system to incorporate a total of 9.3% of the silane quat. A region of homogeneous turbidity was seen along the AES30-Neodol 25-7 side, but the system largely remained one phase.

Example 12

Information from the phase behavior studies was used to formulate a number of compositions. The compositions included both AES12 and AES30, and corresponded to compositions in the phase studies above that were noted as one phase. However, the level of sodium bicarbonate was increased so that the concentration (with regards to the water component) was about 0.07M, or about 0.5 wt. %. Corresponding samples containing no AEM 5772 were also prepared for control studies. All formulas are shown below (surfactants, NaHC03, and water on an active basis, AEM as is).

| AES12 Systems | | | | | | |
|---|---|---|---|---|---|---|
| Sample No. 12- | AES12 | Neodol25-7 | C12AO | NaHC03 | AEM5772 | Deionized H2O |
| 1 | 3.00 | 3.00 | 9.00 | 0.50 | 4.90 | 79.60 |
| 2 | 1.50 | 1.50 | 12.00 | 0.50 | 4.90 | 79.60 |
| 3 | 2.25 | 9.00 | 3.75 | 0.50 | 4.90 | 79.60 |
| 4 | 1.35 | 5.40 | 8.25 | 0.50 | 4.90 | 79.60 |
| 5 | 0.75 | 3.00 | 11.25 | 0.50 | 4.90 | 79.60 |
| 6 | 3.00 | 3.00 | 9.00 | 0.50 | | 84.50 |
| 7 | 1.50 | 1.50 | 12.00 | 0.50 | | 84.50 |
| 8 | 2.25 | 9.00 | 3.75 | 0.50 | | 84.50 |
| 9 | 1.35 | 5.40 | 8.25 | 0.50 | | 84.50 |
| 10 | 0.75 | 3.00 | 11.25 | 0.50 | | 84.50 |

| AES30 Systems | | | | | | |
|---|---|---|---|---|---|---|
| Sample No. 30- | AES30 | Neodol25-7 | C12AO | NaHC03 | AEM5772 | Deionized H2O |
| 1 | 3.00 | 3.00 | 9.00 | 0.50 | 4.90 | 79.60 |
| 2 | 1.50 | 1.50 | 12.00 | 0.50 | 4.90 | 79.60 |
| 3 | 2.25 | 9.00 | 3.75 | 0.50 | 4.90 | 79.60 |
| 4 | 1.35 | 5.40 | 8.25 | 0.50 | 4.90 | 79.60 |
| 5 | 0.75 | 3.00 | 11.25 | 0.50 | 4.90 | 79.60 |
| 6 | 3.00 | 3.00 | 9.00 | 0.50 | | 84.50 |
| 7 | 1.50 | 1.50 | 12.00 | 0.50 | | 84.50 |
| 8 | 2.25 | 9.00 | 3.75 | 0.50 | | 84.50 |
| 9 | 1.35 | 5.40 | 8.25 | 0.50 | | 84.50 |
| 10 | 0.75 | 3.00 | 11.25 | 0.50 | | 84.50 |

All systems were clear and one phase, except sample No. 12-3, which was turbid and homogeneous.
Fabric Treatment Studies In order to treat fabric swatches (cotton 400, approximately 2"×3"), the compositions were diluted to 0.1% in deionized water (Ig of each in 999 g of water). The dilutions were then placed in the buckets of a Tergo-tometer[1]. The solutions were pre-heated to about 88° F. (the target wash temperature). The solutions in the terg buckets were then allowed to equilibrate with the terg bath to a temperature of 88±1° F. The terg timer was then set at 11 minutes. The terg was started (100 rpm), and with 10 minutes remaining, four swatches were added to each bucket. At the end of the wash period, the solutions were removed, and fresh water (990 mL) was placed in each bucket. The temperature was equilibrated at 88° F., and the timer was set for 6 minutes. The terg was started, and with 5 minutes remaining, the swatches were added to each bucket. At completion of this rinse period, the swatches were removed, squeezed dry, and further dried with a heat gun.

[1]Instrument Marking Services, Inc. (Fairfield, N.J.), Terg-O-Tometer Model 7243ES Manual.

Two methods were employed to assess the level of silane quat deposition on each swatch. In the first method, an anionic dye, bromophenol blue (BPB) was used to treat each swatch. The anionic charge on the BPB allows it to bind to the cationic AEM molecule. Treatment was performed by preparing a 0.025% (w/w) solution of BPB in water. The swatches were then soaked in the BPB solution for 20 minutes. The swatches were then removed and rinsed with copious amounts of water.

The level of BPB adsorbed, corresponding to the level of blue color retained on each swatch were assessed by reading each swatch with a colorimeter (BYK Gardner Color-view spectrophotometer). A value of b, or the degree of blue color lying in the CIE L*a*b* color space[2] was then obtained. This value of b was referenced against the value of b for the non-treated white swatch. A value of $\Delta b$, or the change in color, was then calculated:

$$\Delta b = b \text{ (BPB-treated swatch)} - b \text{(non-treated swatch)}$$

As $\Delta b$ decreases, the color becomes more blue.

[2]HunterLab, Application Note Vol. 8, No. 7, July 1996.

In order to correlate $\Delta b$ values with the actual level of quat deposition, standard swatches were prepared where solutions of AEM 5772 with known quat concentrations were applied to the swatch. These standards were then dried with a heat gun and dyed with BPB solution. The dyed areas were then quantified so that values of μg quat/cm$^2$ could be tabulated. The standard swatches were evaluated via the colorimeter to obtain $\Delta b$ values.

The data showed that some dying occurred for samples where no quat was present. In the staining studies performed on the standard swatches, it was generally found that the level of blue staining was linearly dependent on the level of cationic species on the surface.

The level of deposition was calculated to be around 20-25 μg quat/cm$^2$ for all AES-12 and AES-30 samples.

The level of deposition was also investigated via x-ray photoelectron spectroscopy (XPS). Swatches were evaluated using an analysis area of 2 mm×0.8 mm. The level of analysis depth was estimated to be about 50-100 Å. The element Si was used as a tag for the quat, as the quat would have been the only source. Levels of Si, normalized to 100% of the elements detected, are shown below:

| Sample | System | % Si |
|---|---|---|
| 12 | AES12 | 0.5 |
| 12 | AES12 | 0.4 |
| 12 | AES12 | 0.4 |
| 12 | AES12 | 0.4 |
| 12 | AES12 | 0.4 |
| 30 | AES30 | 0.5 |
| 30 | AES30 | 0.5 |
| 30 | AES30 | 0.4 |

-continued

| Sample | System | % Si |
|---|---|---|
| 30 | AES30 | 0.5 |
| 30 | AES30 | 0.5 |

The XPS data confirmed that quat had adsorbed to the surface. It was also consistent with trends observed in the BPB study, in that levels were similar from sample to sample.

The invention claimed is:

1. An article comprising a textile coated with an aqueous composition comprising an alkali metal bicarbonate and a silane quaternary ammonium compound present in amounts of from about 0.3 to 5.0 percent by weight relative to the weight of the aqueous composition.

2. The article of claim 1 comprising a fiber or fabric.

3. The article of claim 1, wherein said composition further comprises a nonionic surfactant.

4. The article of claim 1, wherein the alkali metal bicarbonate is sodium bicarbonate or potassium bicarbonate.

5. The article of claim 2, wherein said alkali metal bicarbonate is present in amounts of from about 0.1 to 10 percent by weight relative to the weight of the aqueous composition.

6. The article of claim 1, wherein the water content of said aqueous composition is from about 80 to 99 weight percent.

7. The article of claim 3, wherein said non-ionic surfactant comprises an ethoxylated alcohol.

8. The article of claim 1, wherein said silane quaternary ammonium compound comprises 3-(trimethoxysilyl)propyloctadecyldimethyl ammonium chloride.

9. The article of claim 1, comprising 10 to 250 wt. % of said aqueous composition on a wet basis.

10. The article of claim 1, further including textile processing aids comprising a mixture of fatty alcohol ethoxylates and a cationic surfactant.

11. The article of claim 1, wherein said composition further includes an anionic surfactant.

12. An article comprising a textile coated with a composition comprising a silane quaternary ammonium compound present in amounts of from about 0.3 to 5.0 percent by weight relative to the weight of the aqueous composition, an alkali metal bicarbonate and a nonionic surfactant, wherein the weight ratio of said silane quaternary ammonium compound to said nonionic surfactant ranges from about 10:1 to 1:<3.0.

13. The article of claim 12, wherein said textile is a fiber or fabric.

14. The article of claim 12, wherein said silane quaternary ammonium compound is 3-(trimethoxysilyl)propyloctadecyldimethyl ammonium chloride.

15. The article of claim 12, wherein said textile comprises a synthetic fiber.

16. The article of claim 12, wherein said textile comprises a natural fiber.

17. The article of claim 12, comprising a coated fabric.

18. The article of claim 12, wherein said alkali metal bicarbonate is sodium bicarbonate or potassium bicarbonate.

19. The article of claim 12, wherein said nonionic surfactant is an ethoxylated alcohol.

20. The article of claim 12, wherein said composition further includes an anionic surfactant.

21. The article of claim 20, wherein said anionic surfactant is a laureth sulfate having at least 12 ethoxy groups.

22. The article of claim 12, further including a laureth sulfate having 12 to 30 ethoxy groups.

23. The article of claim 11, wherein said anionic surfactant comprises alkylether fatty alcohol sulfates wherein said fatty alcohol has at least 12 carbon atoms and contains at least 12 alkoxy groups.

24. The article of claim 23, wherein said anionic surfactant comprises laureth-12 sulfate.

25. The article of claim 23, wherein said anionic surfactant comprises laureth-30 sulfate.

26. An article comprising a textile coated with an aqueous composition prepared by the method comprising:
 a) admixing an effective amount of an alkali metal bicarbonate and a silane quaternary ammonium compound in the presence of water such that the silane quaternary ammonium compound is present at a concentration of from about 0.3 to 5.0 percent by weight relative to the weight of the aqueous composition;
 b) applying the aqueous composition to the textile; and
 c) allowing the aqueous composition to dry so that the silane quaternary ammonium compound binds to the surface of the textile.

* * * * *